United States Patent [19]

Lotsof

[11] Patent Number: 5,026,697

[45] Date of Patent: Jun. 25, 1991

[54] RAPID METHOD FOR INTERRUPTING OR ATTENUATING THE NICOTINE/TOBACCO DEPENDENCY SYNDROME

[75] Inventor: Howard S. Lotsof, Staten Island, N.Y.

[73] Assignee: NDA International, Inc., Staten Island, N.Y.

[21] Appl. No.: 530,263

[22] Filed: May 30, 1990

[51] Int. Cl.$^5$ ............................................. A61K 3/55
[52] U.S. Cl. ................................................... 514/214
[58] Field of Search ................................. 514/813, 214

Primary Examiner—Stanley J. Friedman

[57] ABSTRACT

The administration to a nicotine or tobacco addict of ibogaine, ibogamine or tabernanthine or non-toxic salts of those alkaloids, of the family apocynaceae, has been discovered to interrupt the physiological and psychological aspects of nicotine or tobacco dependency. A single treatment or series of treatments may be effective for one to eighteen months or longer. Treatment consists of the oral, rectal infusion or suppository administration of ibogaine, ibogamine, tabernanthine or their salts in dosage ranges of 1 mg/kg to 60 mg/kg.

10 Claims, No Drawings

RAPID METHOD FOR INTERRUPTING OR ATTENUATING THE NICOTINE/TOBACCO DEPENDENCY SYNDROME

BACKGROUND OF THE INVENTION

The present invention relates generally to improvements in the treatment of nicotine dependency and addiction and relates particularly to an improved method for interrupting the physiological and psychological aspects associated with tobacco or nicotine dependency.

Many procedures and regimes have hertofore been employed and proposed for the treatment of nicotine or tobacco dependency, but these when applied to nicotine and tobacco dependency and addiction, possess numerous drawbacks and disadvantages. The procedures are long, frequently unreliable, generally ineffective when used in the treatment of the hard core nicotine/tobacco addict and may require the self administration of nicotine, nicotine substitutes or anxiolytics.

HISTORICAL BACKGROUND

Ibogaine is one of at least 12 alkaloids found in the Tabernanthe iboga plant of West Africa. The Gabonese as well as, Africans in other countries on that continent have used the drug in the Bwiti religion and Mbiri medical societies, principally, during the last century. Ethnographic studies have been performed by two principal specialists: Otto Gollnhofer and James W. Fernandez. Gollnhofer's works include "Rites of passage in the Bwiti initiation society among the Mitsogo: The chewing of Iboga"; Doctoral Thesis, 3rd cycle, Rene Descartes University, Paris V, January 1974 as well as "Iboga, an African psyuchotropic agent", Psychrotrope, vol. 2, No. 3, 1985 and "Ritual Uses of Iboga in Gabon", ibid vol. 2, No. 3, 1985. Fernandez's book, one of the few in English, "Bwiti—An Ethnography of Religious Imagination in Africa" (Princeton Press, 1982) offers an in depth view of the Bwiti religion among the Fang peoples of Gabon.

One of the first European references to the drug was made by Professor Baillon at the Mar. 6th, 1889 session of the Linnaen Society in Paris during which he described samples obtained by Griffon de Bellay from Gabon and the French Congo.

Early isolation and identification of ibogaine was accomplished by Dybowski and Landrin (Compt. rend. ac. sc. 133:748, 1901); Haller and Heckel (ibid. 133:850); Lambert and Heckel (ibid. 133:1236 and Landrin (Bull. sc. pharm. 11:1905).

Interest in the drug seemed to lie fallow until it was picked up by Raymond-Hamet and his associate E. Rothlin. Raymond-Hamet published the "Effects Of Ibogaine On The Isolated Rabbit Uterus" in 1938 (Compt. rend. soc. biol. 127:592-4). Raymond-Hamet continued to study the drug for a period of 22 years. He singularly published 9 papers: Pharmacological Action Of Ibogaine (Arch. intern. pharmacodynamie, 63:27-39, 1939), Two Physiological Properties Common To Ibogaine And Cocaine (Compt. rend. soc. biol. 133:426-9, 1940), Ibogaine and Ephedrine (Ibid. 134:541-4, 1940), Difference Between Physiological Action of Ibogaine And That Of Cocaine ((Ibid. 211:285-8, 1940), Mediate And Intermediate Effects Of Ibogaine On The Intestine (Compt. rend. soc. biol. 135:176-79, 1941), Pharmacological Antagonism Of Ibogaine (Compt. rend. 212:768-771, 1941), Some Color Reactions Of Ibogaine (Bull. soc. chim. biol. 25:205-10, 1943), Sympathicosthenic Action Of Ibogaine On The Vessels Of The Dog's Paw (Compt. rend. 233:757-58, 1946), and Interpretation Of The Ultraviolet Absorption Curves Of Ibogaine And Tabernanthine (Ibid. 229:1359-61, 1949).

A good source of botanical, pharmacological and toxicological data coming out of this historical period can be found in Jean Delourme-Houde's Thesis (Etude de l'Iboga, University of Paris, 1943). Still another researcher Vincent, D. began his work on ibogaine by a collaboration with Sero, I.: Inhibiting Action Of Tabernanthe Iboga on Serum Cholinesterase (Compt. rend. soc. biol. 136:612-14, 1942). Vincent participated in the publication of Five other papers: The Ultraviolet Absorption Spectrum Of Ibogaine (Brustier, B., Vincent, D. and Sero, I., Compt. rend. 216:909-911, 1943), Detection Of Cholinesterase Inhibiting Alkaloids (Vincent, D. and Beaujard, P, Ann. pharm. franc. 3:22-26, 1945), The Cholinesterase Of The Pancreas: Its Behavior In The Presence Of Some Inhibitors In Comparison With The Cholinesterases Of Serum And Brain (Vincent, D. and Lagreau, P., Bull. soc. chim. biol. 31:1043-45. 1949); and two papers which he and Ramond-Hamet worked on together: Action Of Some Sympathicosthenic Alkaloids On The Cholinesterases (Compt. rend. soc. biol. 150:1384-86, 1956) and On Some Pharmacological Effects Of Three Alkaloids Of Tabernanthe Iboga, Baillon: Ibogaine, Iboluteine And Tabernanthine (Compt. rend. soc. biol. 154:2223-27, 1960).

Another of the French chemists to provide substantial information on ibogaine has been Dr. Robert Goutarel, considered by two generations of French chemists to be the "father of ibogaine research". Goutarel's work includes Structure of Ibogaine (Goutarel, R.; Janot, M. and M.; Mathys, F and Prelog, V.: Compt. rend, ac. sc., 237:1718, 1953), Research on some indole alkaloids and their relations with the metabolism of tryptophan and dihydroxyphenylalanine, ibid 237:1718, 1954 and U.S. Pat. No. 2,813,873 (Nov., 19, 1957) Derivatives of the ibogaine alkaloids.

The structure of ibogaine was also investigated by Dickel et al (J.A.C.S. 80:123, 1958). The first total synthesis was cited by Buchi et al. (J.A.C.S. 87:2073, 1965) and (Ibid. 88, 3099, 1966).

In 1956 Salmoiraghi and Page elucidated ibogaine's relations to serotonin (J. Pharm. and expt. ther. 120(1):20-25, 1957.9). About the same time J. A. Schneider published three important papers. The first, Potentiation Action Of Ibogaine On Morphine Analgesia was done in collaboration with Marie McArthur (Experiential 12:323-24, 1956). The second was Neuropharmacological Studies Of Ibogaine: An Indole Alkaloid With Central Stimulant Properties (Schneider, J. A. and Sigg, E. B. Ann. of N.Y. acad. of sciences, 66:765-76, 1957) and third was An Analysis Of The Cardiovascular Action Of Ibogaine HCl (Schneider, J. A. and Rinehard, R. K., Arch. int. pharmacodyn. 110:92-102, 1957).

Ibogaine's stimulant properties were further investigated by Chen and Bohner in A Study Of Central Nervous System Stimulants (J. Pharm and expt. ther. 123(3):212-215, 1958). Gershon and Lang published A Psychological Study Of Some Indole Alkaloids (Arch. intern. pharmacodynamie, 135:31-56, 1962).

R. D. Bunag evaluated certain aspects of the relationship between ibogaine and Substance P (Bunag, R. D., Walaszek, E. J., The Cardiovascular Effects Of Substance P In The Chicken, Ann. N.Y. Acad. sci. 104(1):437-48, 1963).

Claudio Naranjo reported on the effects of ibogaine on human subjects in his paper, Psychotherapeutic Possibilities Of New Fantasy-Enhancing Drugs (Clinical Toxicology 2(2):209-224, June 1969).

Dhahir, H.I. published a good review of the pharmacology and toxicology of ibogaine in his Doctoral Thesis, A Comparative Study Of The Toxicity Of Ibogaine And Serotonin (University Microfilms International 71-25-341, Ann Arbor, Mich.). The paper gives an overview of much of the work accomplished with ibogaine.

Additional studies of interest include: The Effects Of Some Hallucinogens On Aggressiveness Of Mice And Rats (Kostowski et al., Pharmacology 7:259-63, 1972), Cerebral Pharmacokinetics Of Tremor-Producing Harmala And Iboga Alkaloids (Zetler et al., Pharmacology 7(4):237-248, 1972), High Affinity 3H-Serotonin Binding To Caudate: Inhibition By Hallucinogenic And Serotonergic Drugs (Whitaker, P. and Seeman, P., Psychopharmacology 59:1-5, 1978), Selective Labeling Of Serotonin Receptors by d-(3H) Lysergic Acid Diethylamide In Calf Caudate (Proc. natl. acad. sci., U.S.A. 75(12):5783-87, Dec. 1978) and A Common Mechanism Of Lysergic Acid, Indolealkylamine And Phenethylamine Hallucinogens: Serotonergic Mediation Of Behavioral Effects In Rats (Sloviter, R. et al., J. Pharm. and expt. ther. 214(2):231-38, 1980). The most current work has been performed by Dzoljic, M. R.; Dzoljic E. D. and Kaplan, C. D. (Effect of Ibogaine on Naloxone-Precipitated Withdrawal Syndrome in Chronic Morphine dependent Rats, Arch. Int. Pharmacodyn., 294:64-70, 1988.)

SUMMARY OF THE INVENTION

It is the principal object of the present invention to provide an improved method of treatment for cases of nicotine/tobacco dependency.

Another object of the present invention is to provide an improved method for lessening the physiological and psychlological aspects of nicotine/tobacco deprivation and withdrawal in the addict/abuser.

Still another object of the present invention is to provide a method of the above nature characterized by its high degree of success, the absence of the great pain and discomfort accompanying earlier treatments, the ease and convenience of application, the absence of undesirable or persistent side effects and the long term effectiveness of the treatment.

The above and other objects of the present invention will become apparent from a reading of the following description which sets forth preferred embodiments thereof.

A feature of the present invention is based on the discovery that an alkaloid of the family Apocynaceae and its therapeutically active derivatives and salts, particularly ibogaine, ibogamine, tabernanthine and their therapeutically active, non-toxic derivatives and salts for example, ibogaine, tabernanthine or ibogamine hydrochloride and other non-toxic salts of those alkaloids, possess the unexpected unique ability to interrupt nicotine/tobacco dependency. Examples of other salts or forms of ibogaine, ibogamine or tabernanthine which may be used are the hydrobromide, tannate, ibogaine base, and any other non-toxic salt or form of the given alkaloids.

For the purpose of definition, the nicotine or tobacco dependency syndrome is meant to consist of all the symptomology demonstrated by addicts in their use of and craving for nicotine and/or tobacco.

A single treatment or series of treatments of ibogaine, tabernanthine or ibogamine or their salts in doses ranging from 1 mg/kg to 60 mg/kg, administered orally or rectally, interrupted the use of nicotine and/or tobacco dependency. Studies in the rat have shown the most efficacious doses to be 40 mg/kg to 60 mg/kg, but the dose can be within the range of 1-60 mg/kg.

In the administration of acceptable dosage forms, any of a variety of preparations may be compounded, for example: capsules, tablets, pills, powder, solutions, injections or suppositories, etc. In addition to the active agent, there may be present additional substances used in the manufacture of pharmaceutical preparations such as binders, fillers and other inert ingredients.

The advantage of this invention is that it allows for the rapid interruption of physical and psychological withdrawal symptoms associated with nicotine/tobacco use.

The following examples are given by way of illustration of the present and improved method of treating nicotine abuse or dependency and are not intended to limit the scope of the present invention.

EXAMPLE 1

Subject, age 42, was smoking two or more packs of filter cigarettes per day. Subject was administered a single dose of 15 mg/kg of ibogaine. Subject suffered no nicotine withdrawal and has not smoked cigarettes for more than 24 months, at which time tracking ceased.

EXAMPLE 2

Subject, age 34, Subject was smoking one and a half packs of filter cigarettes per day when administered 15 mg/kg of ibogaine HCl. Cigarette smoking continued, but diminished over a thirty day period at which time the subject ceased to smoke cigarettes and maintained this state for sixty days, at which time tracking was discontinued.

EXAMPLE 3

Subject, a 36 year old male had been smoking four to six cigerettes a day for a year. A single treatment with 25 mg/kg of ibogaine interrupted all tobacco use. Subject has had no desire to continue smoking and suffered no discomfort of nicotine withdrawal. Tracking was discontinued after sixty days.

While there have been described preferred embodiments of the present invention, it is apparent that numerous alterations, omissions and additions may be made without departing from the spirit thereof.

I claim:

1. A method for treating nicotine/tobacco dependency comprising internally administering to a person in need of such treatment an effective amount of at least one member of the group consisting of Apocynaceae alkaloids and physiologically acceptable salts thereof.

2. The method of claim 1 wherein said alkaloid is selected from the group consisting of ibogaine, tabernanthine and ibogamine.

3. The method of claim 1 wherein said at least one member is a pharmceutically acceptable said of said alkaloid.

4. The method of claim 3 wherein said at least one member is selected from the group of hydrochloride, tartrate, hydrobromide and tannate salts of ibogaine, tabernanthine and ibogamine.

5. The method of any of the claims 2-4 comprising oral administration of said at least one member.

6. The method of any one of the claims 2-4 comprising rectal administration of said at least one member.

7. The method of any one of claims 2-4 comprising a single repeated administration of said at least one member wherein successive administrations are spaced apart a plurality of days or hours and wherein said effective amount is administered in one or in a plurality of dosages.

8. The method of any one of claims 2-4 wherein said amount is within the range of from 1 mg/kg to 60 mg/kg.

9. The method of claim 7 wherein the amount administered each time is within the range of 1 mg/kg-60 mg/kg.

10. The method of claim 1 wherein said alkaloid is administered in a dosage form selected from the group consisting of pills, tablets, capsules, oral liquids, suppositories and rectal infusions. rectal infusions.

* * * * *